| United States Patent [19]
Parish

[11] 4,002,761
[45] Jan. 11, 1977

[54] 2,3-BIS-(3-LOWER ALKANOYL-2-THIOUREIDO)-PYRIDINES

[75] Inventor: Roger C. Parish, King of Prussia, Pa.

[73] Assignee: SmithKline Corporation, Philadelphia, Pa.

[22] Filed: Feb. 10, 1976

[21] Appl. No.: 657,016

Related U.S. Application Data

[62] Division of Ser. No. 565,026, April 3, 1975, Pat. No. 3,961,063.

[52] U.S. Cl. .................. 424/263; 260/294.8 F; 260/294.8 G; 260/294.8 H
[51] Int. Cl.² ............ A61K 31/395; C07D 213/53
[58] Field of Search ............. 260/294.8 H; 424/263

[56] References Cited

UNITED STATES PATENTS 3,590,045  6/1971  Vogt .................. 260/295 CA

OTHER PUBLICATIONS

Tisler et al., Chem. Abstracts, vol. 79, 105,126e (1973).
Toldy et al., Chem. Abstracts, vol. 71, 60,989e (1969).

Primary Examiner—Alan L. Rotman
Attorney, Agent, or Firm—William H. Edgerton; Alan D. Lourie; Richard D. Foggio

[57] ABSTRACT

New 2,3-bis-(3-acyl-2-thioureido)-pyridines having anthelmintic activity are prepared by reacting a diaminopyridine with acylthiocyanates.

6 Claims, No Drawings

2,3-BIS-(3-LOWER ALKANOYL-2-THIOUREIDO)-PYRIDINES

This application is a divisional application of copending Ser. No. 565,026 filed Apr. 3, 1975, now U.S. Pat. No. 3,961,063.

This invention relates to new 2,3-bis-(3-acyl-2-thioureido)-pyridines, a new class of chemical compounds, which have therapeutic activity, especially as anthelmintic and fungicidal agents.

The compounds are illustrated by the following structural formula:

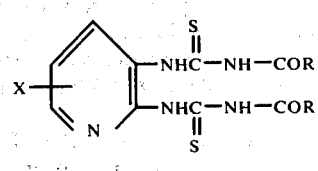

FORMULA I in which R is lower alkyl or preferably lower alkoxy or heterocyclyl such as 2-thienyl or 2-furyl; and X is hydrogen, lower alkyl, trifluoromethyl, halo such as chloro, bromo or fluoro, lower alkoxy, benzoyl, lower alkylthio, lower alkylsulfonyl, phenyloxy or phenylthio.

In Formula I, preferred compounds are those in which X is hydrogen, butyl, propylthio, phenylthio or propyloxy in the 5-position; and R is methyl, ethyl, methoxy, ethoxy, 2-furyl or 2-thienyl.

The terms "lower alkyl" or "lower alkoxy" are alicyclic, branched or straight alkyl moieties, for convenience limited to a carbon range of 1–6 carbons, such as methyl, ethyl, propyl, isopropyl, butyl, hexyl, isoamyl, cyclopropylmethyl, cyclohexyl, cyclopentyl or their corresponding lower alkyloxy or lower alkylthio congeners. Most useful are 3–4 carbon containing moieties as the nuclear substituents (X) and 1–4 carbon containing moieties in the acyl function (R). The term heterocyclyl is most conveniently a pyridyl, 2-furyl or 2-thienyl although other convenient heterocyclic moieties in the RCONHCS- "leaving groups" may be used. The term "leaving group" is known in organic chemistry and its meaning is clear to those skilled in the art.

The prior art, to my knowledge, does not describe the new compounds described here. Certain 2-acylthiourea substituted pyridines are described for use in other therapeutic fields (C.A. 79, 105126e; C.A. 74, 76202r; C.A. 71, 60989e; C.A. 77, 114365t). Other nonacylthioureapyridines are also described (C.A. 78, P84261g; C.A. 78, 147820m). No 2,3-thioallophanate substituted pyridines are known to my knowledge and certainly no 2,3,5-substituted compounds which comprise the preferred subgenus of this invention. The adjacent 3-acyl-2-thioureido substituents of the compounds of this invention are essential for the anthelmintic utility of the compounds.

The new compounds of this invention are prepared by reaction of a 2,3-diaminopyridine with an acylthiocyanate, R—CO—NCS, which in turn is prepared as known to the art from an acyl chloride and an alkali or ammonium thiocyanate. The basic reaction is run to completion in a nonreactive solvent in which the reactants are soluble, most suitable in acetone usually at about 01–25° C., preferably at about 10° C. to room temperature.

For convenience the acylthiocyanate is most often prepared in the same solvent as the reaction with the diamine so that the intermediate thiocyanate need not be isolated.

The pyridinediamine starting materials are prepared by most reactions known to the art. Many of the diamines are known, see for example U.S. Pat. No. 3,590,045; Netherlands Pat. No. 73/08294; France Pat. No. 1,447,539 and Belgium Pat. No. 668,739. Others are prepared by chemical or preferably catalytic reduction of the 2-amino-3-nitropyridines. The latter may in turn be prepared by rearrangement of the pyridine-2-nitramino congener. Reference may be made to Chapter IX of "Pyridine and its Derivatives", part 3, Interscience 1962; J. Chem. Soc., 1948, 138g; or J. Chem. Soc., 1948, 1389. It will be appreciated that the rearrangement of a 2-nitraminopyridine will proceed to the 3-nitro most advantageously when the appropriate blocking substituent is present at position 5.

The compounds represented by Formula I are anthelmintic agents to be used against parasites of warm blooded animals, including both mature and immature parasitic forms. In particular, these compounds have high activity against various helminthic infections of the intestinal tract of economically important animals, coupled with low systemic toxicity to the host animal.

The compounds of Formula I are most efficacious against parasitic gastroenteritis in sheep, such as *Haemonchus contortus*, *Ostertagia spp.*, *Trichostrongylus spp.*, *Nematodirus spp.*, *Trichuris ovis*, *Cooperia spp.* and *Strongyloides papillosus*. *Bunostomum trigonocephalum* and *Oesophagostomum spp.* are other important parasites of sheep.

Animals of low weight are treated with unit doses ranging no higher than a few milligrams; whereas animals of high body weight, such as ruminants, require proportionately larger unit doses ranging up to several grams. Preferably, a single dose is administered daily for each animal species based on the weight of that species.

The amount of ingredient administered will depend on the weight of the host, but will usually be between about 1 mg./kg. and 300 mg./kg. of body weight daily.

In practice, an active compound of the structure of Formula I is usually formulated with a nontoxic carrier therefor to give anthelmintic compositions of this invention. The carrier may be an orally ingestible container for the active ingredient, for example, a hard or soft gelatin capsule; or it may be a pharmaceutically acceptable diluent or excipient of the kind normally used in the production of medicaments, for example maize starch, terra alba, lactose, sucrose, calcium phosphate, gelatin, talcum, stearic acid, magnesium stearate, dextrin, agar, pectin or acacia.

Exemplary of liquid carriers are peanut oil, olive oil, sesame oil and water. Similarly, the carrier or diluent may include a time delay material such as glyceryl monostearate or glyceryl distearate alone or with a wax.

A wide variety of pharmaceutical forms can be employed, such as suspensions, drench powders, packaged powders, boluses, capsules. Thus, if a solid carrier is used, the preparation can be tableted, placed in a hard gelatin capsule, compounded in the form of a troche or lozenge or suspended in a powder carrier. The amount of solid carrier will vary widely but preferably will be from about 25 mg. to about 3 g. If a liquid carrier is used, the preparation may be in the form of a soft gelatin capsule, placed in an ampoule or in liquid suspension.

The compositions are most often made up in a form suitable for oral administration to animals and may therefore take the form of a bolus or a liquid, for example, an emulsion, a solution or suspension for dispersal, i.e., in water, oil (such as arachis oil) or other liquid. In addition, the compounds of Formula I can be formulated as a feed additive by mixing with a suitable feed such as ground soybean meal, soybean oil, etc.

As previously mentioned, the compounds of Formula I have general anthelmintic activity and accordingly a further and most important aspect of this invention provides a method of combatting helminthic infections in an animal afflicted with or susceptible to such infections which comprises administering, usually orally, to the animal in a sufficient nontoxic, but effective, dose an anthelmintic compound falling within the definition of Formula I, generally in the form of a pharmaceutical or veterinary composition as hereinabove described. The daily dose range commonly used is from about 1 mg./kg. to about 300 mg./kg., preferably about 3 mg./kg. to 50 mg./kg., depending on the species of host and regimen used. One dose per day administration is preferred but up to five of the dosage units described above may be used if desired. The daily dose range is therefore identical to the dosage unit range.

Exemplary of the pharmaceutical or veterinary compositions are a bolus containing from 5 to 25%, preferably about 10% of the active ingredient of Formula I, a drench suspension containing from 5 to 30%, preferably about 5% of the active component and a feed additive containing from 15 to 30%, preferably about 25% of a compound of Formula I.

The anthelmintic preparations are made following the conventional techniques of the pharmaceutical chemist involving mixing, granulating and compressing when necessary or variously mixing and dissolving the ingredients as appropriate to the desired end product.

When tableting is used, the resulting tablets may be then coated with methyl methacrylate to form an enteric coating, i.e., a coating which is substantially insoluble in gastric secretions but substantially soluble in intestinal fluids.

The compositions thus prepared are administered, usually orally, to an infected or susceptible host from one to five times daily for curative or prophylactic anthelmintic activity.

The compounds of Formula I are also antifungal agents, being formulated and used in the manner known to the art for related antifungal compounds.

The following examples illustrate the invention but are not to be construed as limiting the scope thereof. For example, another X may be present in the pyridine ring to give tetrasubstituted compounds but these usually offer little advantage over the di- or trisubstituted pyridines of Formula I.

EXAMPLE 1

2-Furoylisothiocyanate is prepared from 2-furoyl chloride (13 g., 0.1 moles) and potassium thiocyanate (9.7 g., 0.1 moles) in acetone (35 ml.). The mixture is stirred at 10° C. for fifteen minutes. 2,3-Diaminopyridine (2.8 g., 0.0257 moles) is added as a solid, the mixture stirred at 10° C. and allowed to warm to room temperature for three hours. The yellow solid is filtered, washed with acetone, slurried in 500 ml. water, filtered, washed with water and air dried. The product, 8.45 g. (80%) is purified by recrystallization from acetone giving 6.1 g. (57%) of desired product, as yellow crystals, m.p. 174° C. dec., of 2,3-bis[3-(2-furoyl)-2-thioureido]pyridine.

EXAMPLE 2

Ethoxycarbonylisothiocyanate is prepared from ethyl chloroformate (10.85 g., 0.1 moles) and potassium thiocyanate (9.7 g., 0.1 moles) in acetone (35 ml.). The mixture is warmed at 35° C. for 30 minutes with stirring. 2,3-Diaminopyridine (4.25 g., 0.039 moles) dissolved in 50 ml. acetone is added and the mixture stirred at room temperature overnight. The mixture is filtered and the filtrate poured into water (500 ml.). The precipitated solid is filtered, air dried, and recrystallized from ethanol giving desired product, 4.85 g. (33%), m.p. 164° C., dec., of 2,3-bis-(3-ethoxycarbonyl-2-thioureido)-pyridine.

The reaction is also run replacing the ethyl chloroformate with an alkanoyl halide, such as propionyl chloride to give the 2,3-bis-(3-propionyl-2-thioureido)-pyridine.

EXAMPLE 3

Using methyl chloroformate and 2,3-diamino-5-propylthiopyridine prepared from catalytic reduction of the 3-nitro congener prepared similar to 2-amino-5-methyl-sulfonyl-3-nitropyridine (C.A., 76, 81815m) in the reaction of Example 2 gives 2,3-bis-(3-methoxycarbonyl-2-thioureido)-5-propylthiopyridine.

Using 5-butyl-2,3-diaminopyridine in the reaction of Example 1, gives 5-butyl-2,3-bis[3-(2-furoyl)-2-thioureido]pyridine.

Using 2,3-diamino-5-trifluoromethylpyridine in the reaction of Example 2, gives 2,3-bis-(3-ethoxycarbonyl-2-thioureido)-5-trifluoromethylpyridine.

Using 2,3-diamino-5-propylpyridine gives 2,3-bis-(3-ethoxycarbonyl-2-thioureido)-5-propylpyridine.

Using 2,3-diamino-6-ethylpyridine gives 2,3-bis-(3-ethoxycarbonyl-2-thioureido)-6-ethylpyridine.

Using 2,3-diamino-4-methylpyridine gives 2,3-bis-(3-ethoxycarbonyl-2-thioureido)-4-methylpyridine.

Using 2,3-diamino-6-butoxypyridine gives 2,3-bis-(3-ethoxycarbonyl-2-thioureido)-6-butoxypyridine.

Using 2,3-diamino-6-bromopyridine gives 2,3-bis-(3-ethoxycarbonyl-2-thioureido)-6-bromopyridine.

Using 2,3-diamino-6-octyloxypyridine gives 2,3-bis-(3-ethoxycarbonyl-2-thioureido)-6-octyloxypyridine.

Using 2,3-diamino-5-chloropyridine gives 2,3-bis-(3-ethoxycarbonyl-2-thioureido)-5-chloropyridine.

Using 2,3-diamino-5-cyclohexylthiopyridine gives 2,3-bis-(3-ethoxycarbonyl-2-thioureido)-5-cyclohexylthiopyridine.

Using propionyl chloride in place of furoyl chloride of Example 1, and using 5-propylthio-2,3-diaminopyridine gives 2,3-bis-(3-propionyl-2-thioureido)-5-propylthiopyridine.

EXAMPLE 4

Using nitration of a 2-aminopyridine to the 2-nitramino derivative, rearrangement in sulfuric acid to the corresponding 2-amino-3-nitropyridine, selective reduction by catalytic hydrogenation using noble metal catalyst to give the diamine then reaction by the procedure of example 2 using an appropriate acyl halide gives the following diamines and the corresponding bis-(3-acyl-2-thioureido)-pyridines:

5-benzoyl-2,3-diaminopyridine and 2,3-bis-(3-methoxycarbonyl-2-thioureido)-5-benzoylpyridine;

4-methylthio-2,3-diaminopyridine and 2.3-bis[3-(2-thienyl)-2-thioureido]4-methylthiopyridine;

5-phenoxy-2,3-diaminopyridine and 2,3-bis-(3-methoxycarbonyl-2-thioureido)-5-phenoxypyridine;

2,3-diamino-5-phenylthio-4-chloropyridine and 2,3-bis-(3-methoxycarbonyl-2-thioureido)-4-chloro-5-phenylthiopyridine.

EXAMPLE 5

| Typical Sheep Drench | % Wt./Vol. |
|---|---|
| 2,3-bis-(3-Ethoxycarbonyl-2-thioureido)-5-n-propoxypyridine | 5.000 |
| Veegum, regular | 0.350 |
| Sodium carboxymethylcellulose, type 7H3SF | 0.264 |
| Glycerin | 5.000 |
| Polysorbate 80 (Tween 80) | 0.800 |
| Sorbitan monolaurate (Span 20) | 0.270 |
| Potassium sorbate | 0.150 |
| Benzoic acid | 0.100 |
| Antifoam AF emulsion | 0.035 |
| Water q.s. ad | 100.000 |

To a volume of water equivalent to 70% of the total product and heated to about 60° C. are added the sodium carboxymethylcellulose and veegum followed by the glycerin. The mixture is stirred and cooled and part of the polysorbate 80 and potassium sorbate are added. The suspending agents are fully hydrated, the benzoic acid, sorbitan monolaurate and 15% more water are added and the mixture is cooled to below 30° C. The remainder of the solid ingredients are then added and the product is thoroughly mixed and deaerated. The solution is brought to volume by addition of water and screened through a No. N20RT screen on a Homoloid mill or other suitable equipment to assure complete dispersion of the drug.

In like manner, the other 2,3-bis-(3-acyl-2-thioureido)-pyridines of Formula I and Examples 1-4 may be formulated as described above.

EXAMPLE 6

| Premix (feed additive) | % Wt./Total Wt. |
|---|---|
| 2,3-bis-(3-Methoxycarbonyl-2-thioureido)-5-phenylthiopyridine | 23.0 |
| Soybean oil with 0.3% ethoxyquin | 3.0 |
| Soybean mill run (reground) | 74.0 |

The soybean mill run and soybean oil with ethoxyquin are mixed until thoroughly dispersed. The 2,3-bis-(3-methoxycarbonyl-2-thioureido)-5-phenylthiopyridine is screened through a 20 mesh screen and added to the mixture. Mixing is continued until the batch is homogeneous.

In like manner, other substituted 2,3-bis-(3-acyl-2-thioureido)-pyridines of this invention may be formulated as premixed feed additives.

What is claimed is:

1. A compound of the formula:

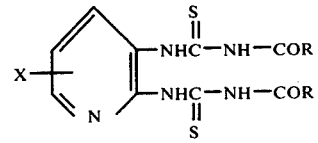

in which R is lower alkyl; and X is hydrogen, lower alkyl, trifluoromethyl, halo, lower alkoxy, benzoyl, lower alkylthio, lower alkylsulfonyl, phenyloxy or phenylthio.

2. A compound of claim 1 in which X is in the 5-position.

3. A compound of claim 2 in which R is lower alkyl.

4. The compound of claim 1 in which X is 5-propylthio and R is ethyl.

5. The method of combatting helminthic infections in warm blooded animals afflicted with or susceptible to helminthic infections, comprising administering orally to said animals an effective but nontoxic quantity of a compound as claimed in claim 1.

6. An anthelmintic composition comprising an anthelmintically effective but nontoxic quantity of a compound as claimed in claim 1, dispersed uniformly throughout an inert carier in amounts selected from the range of 1 to 300 mg./kg. per dosage unit.

* * * * *